(12) United States Patent
Morito et al.

(10) Patent No.: US 8,974,735 B2
(45) Date of Patent: Mar. 10, 2015

(54) AIR PURIFICATION SYSTEM

(75) Inventors: Yuko Morito, Tokyo (JP); Akira Fujishima, Kanagawa (JP)

(73) Assignee: U-Vix Corporation, Tokyo (JP)

( * ) Notice: Subject to any disclaimer, the term of this patent is extended or adjusted under 35 U.S.C. 154(b) by 845 days.

(21) Appl. No.: 13/194,540

(22) Filed: Jul. 29, 2011

(65) Prior Publication Data

US 2012/0121470 A1 May 17, 2012

Related U.S. Application Data

(60) Provisional application No. 61/407,044, filed on Oct. 27, 2010.

(30) Foreign Application Priority Data

Aug. 5, 2010 (JP) .................................. 2010-175999

(51) Int. Cl.
*A62B 7/08* (2006.01)
*A61L 9/20* (2006.01)
(Continued)

(52) U.S. Cl.
CPC . *A61L 9/205* (2013.01); *A61L 9/22* (2013.01); *B01D 53/32* (2013.01); *B01D 53/8634* (2013.01); *B01D 53/8668* (2013.01); *B01D 53/885* (2013.01); *B01J 21/063* (2013.01); *B01J 35/004* (2013.01); *B01J 37/0201* (2013.01); *B01D 2255/20707* (2013.01); *B01D 2257/406* (2013.01); *B01D 2257/704* (2013.01); *B01D 2258/06* (2013.01); *B01D 2259/804* (2013.01);
(Continued)

(58) Field of Classification Search
CPC ............... A61L 2/00; A61L 2/02; A61L 2/08; A61L 2/14; A61L 9/00; A61L 9/16; A61L 9/22; A61L 2202/00; A61L 2202/10; A61L 2202/11; A61L 2202/13; A61L 2209/00; A61L 2209/10; A61L 2209/14; A61L 2209/21; F24F 2003/00; F24F 2003/12; F24F 2003/16; F24F 2003/1635; F24F 2003/1664; F24F 2003/1682; H05H 1/24; H05H 1/2406
USPC .................................................. 422/120–122
See application file for complete search history.

(56) References Cited

U.S. PATENT DOCUMENTS

2,822,327 A * 2/1958 Hammesfahr et al. ........ 204/176
3,967,131 A * 6/1976 Slipiec et al. ............ 422/186.18
(Continued)

FOREIGN PATENT DOCUMENTS

| CN | 1919425 | * | 2/2007 |
| JP | 11-047558 A | | 2/1999 |
| JP | 2001-187319 A | | 7/2001 |

*Primary Examiner* — Monzer R Chorbaji
(74) *Attorney, Agent, or Firm* — Procopio, Cory, Hargreaves & Savitch LLP

(57) ABSTRACT

An air purification system includes an internally hollow cylindrical casing made of a non-conducting material; an inner electrode arranged on an inner surface of the supporting member; an outer electrode arranged on an outer surface of the supporting member; a photocatalyst filter arranged on an outer surface of the outer electrode for purifying air inside a plasma generation zone; and a power source for supplying power of opposite polarities to each of the inner electrode and the outer electrode so as to generate plasma. The photocatalyst filter includes a filter element, and the filter element includes a porous titanium foil having a non-periodic spongy structure impregnated with anatase titanium dioxide particles as a photocatalyst.

4 Claims, 12 Drawing Sheets

(51) Int. Cl.
- *A61L 9/22* (2006.01)
- *B01D 53/32* (2006.01)
- *B01D 53/86* (2006.01)
- *B01D 53/88* (2006.01)
- *B01J 21/06* (2006.01)
- *B01J 35/00* (2006.01)
- *B01J 37/02* (2006.01)
- *F24F 3/16* (2006.01)

(52) U.S. Cl.
CPC ... *B01D 2259/818* (2013.01); *F24F 2003/1635* (2013.01)

USPC .......................... 422/120; 422/121; 422/122

(56) References Cited

U.S. PATENT DOCUMENTS

| | | | | |
|---|---|---|---|---|
| 4,909,996 | A * | 3/1990 | Uys | 422/186.07 |
| 5,409,673 | A * | 4/1995 | Mausgrover et al. | 422/186.07 |
| 7,497,889 | B2 * | 3/2009 | Furukawa et al. | 55/523 |
| 2012/0171079 | A1 * | 7/2012 | Morito et al. | 422/121 |

* cited by examiner

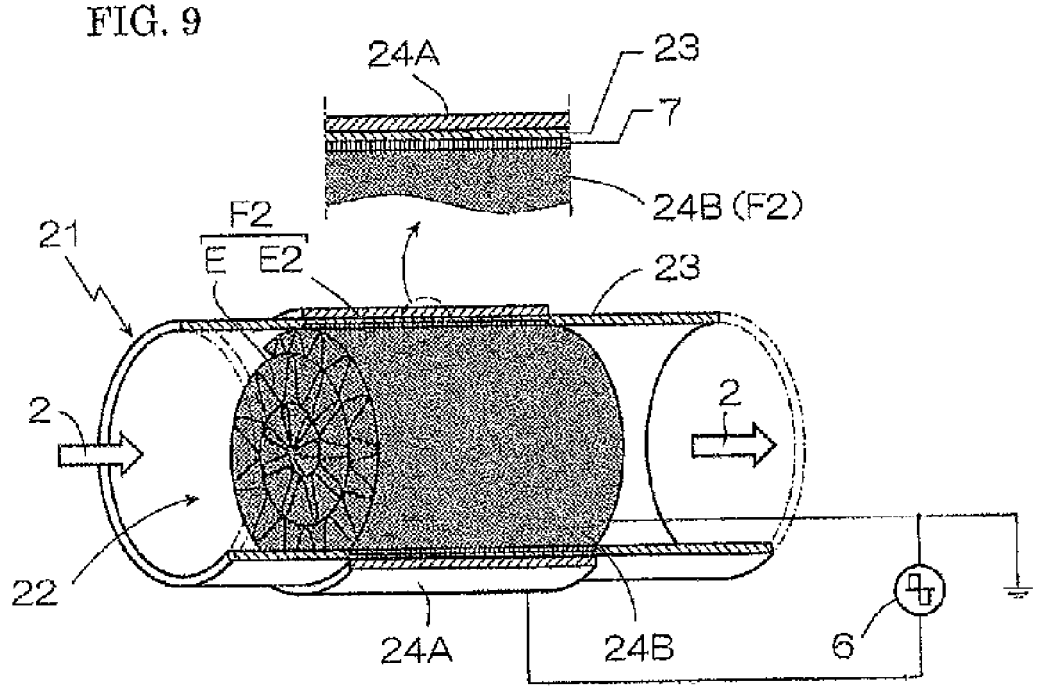

AIR PURIFICATION SYSTEM

TECHNICAL FIELD

Aspects of the inventive concept relate to an air purification system in which a photocatalyst filter is arranged in a plasma generation zone through which air that needs to be purified is passed. The exemplary embodiments relate to an air purification system for mounting in home electric appliances such as refrigerators, air conditioners, vacuum cleaners, humidifiers, and dehumidifiers.

BACKGROUND ART

A photocatalyst-plasma hybrid air purification system that is used for decomposing pollutants in air to purify the air is known in the art. In this photocatalyst-plasma hybrid air purification system, in addition to decomposing the pollutants by the action of plasma at the room temperature and atmospheric pressure, the pollutants are decomposed by a photocatalytic action by exciting titanium oxide, which is a photocatalyst, by plasma emission.

FIG. 21 depicts such a photocatalyst-plasma hybrid air purification system 41. The photocatalyst-plasma hybrid air purification system 41 includes an inner cylindrical electrode 42 and an outer cylindrical electrode 43 with an air space therebetween. A photocatalytic layer is provided on an inner surface of the outer cylindrical electrode 43. The inner cylindrical electrode 42 and the outer cylindrical electrode 43 function as a pair of plasma generation electrodes. Such a photocatalyst-plasma hybrid air purification system is disclosed, for example, in Japanese Patent Application Laid-open No. 2001-187319.

In the conventional photocatalyst-plasma hybrid air purification system, even if a large amount of photocatalytic particles are mixed in the photocatalytic layer, because the air comes in contact only with a surface of the photocatalytic layer, air purification capacity is low. Moreover, due to the position of the photocatalytic layer on the inner surface of the outer cylindrical electrode 43, it is not easy to increase a surface area of the photocatalytic layer, i.e., it is not easy to increase the air purification capacity.

Furthermore, the space between the inner cylindrical electrode 42 and the outer cylindrical electrode 43 cannot be widened; because, if the space is widened, the air that needs to be purified will not efficiently contact the photocatalyst. Because the space is narrow, it is not possible to pass a lot of air through this space.

An air purification system that solves the above problems is disclosed in Japanese Patent Application Laid-open No. H11-47558. As shown in FIG. 22, this air purification system has a wire-shaped high voltage electrode 52 arranged in an insulating cylinder 51 that constitutes an air passage. A grounding electrode 53 is arranged on an outer periphery of the insulating cylinder 51. A photocatalyst member 55 formed by winding a porous photocatalyst sheet 54 is arranged between the high voltage electrode 52 and the grounding electrode 53 while securing an electric discharge space.

The porous photocatalyst sheet 54 is formed in the following manner. A dispersion of anatase titanium dioxide or fluorinated resin, which is a photocatalyst, is applied to a sheet-like porous substrate and dried, or the sheet-like substrate is dipped in the dispersion, and removed from the dispersion and dried. This results in the formation of a film of photocatalyst on the substrate. The substrate can be a nonwoven cloth (a felt) made from glass fiber, ceramic fiber, metallic fiber, and carbon fiber.

CITATION LIST

Patent Literature

Japanese Patent Application Laid-open No. H11-47558.

SUMMARY

Technical Problem

However, a binding between the photocatalyst and the substrate is extremely weak. Therefore, the photocatalyst easily peels off from the substrate in the process of winding the porous photocatalyst sheet, and even when the porous photocatalyst sheet is grasped with a hand to wind it. Thus, the life of the porous photocatalyst sheet is short and it does not efficiently decompose the pollutants.

Generally, corona discharge, glow discharge, or arc discharge needs to be generated when producing plasma. The magnitude of a required electric current increases in order from the corona discharge, glow discharge, and arc discharge. The corona discharge is popular in air purification systems for home use; because, corona discharge can be generated with a smaller electric current, i.e., with a smaller power supply.

Ironically, plasma energy generated by the corona discharge is comparatively small. The small plasma energy cannot decompose pollutants whose molecules or atoms have a stronger bonding energy (BDE) that require relatively higher energy to disaggregate the molecules or the atoms. Consequently, such pollutants remain behind undecomposed and lead to degradation of the processing efficiency of the air purification system.

Plasma energy generated by the arc discharge is larger, and this plasma has a higher decomposition power. However, the required electric current is also larger and a larger power supply is required to produce the larger electric current. Consequently, the arc discharge is not suitable for use in air purification systems for mounting in home electric appliances.

If the air purification system is made small to the extent that it can be mounted in home electric appliances, a plasma generation zone where the air is actually purified also becomes small leading to a degradation of the processing efficiency of the air purification system.

Thus, there is a need and room for improvement in the conventional technology.

BRIEF DESCRIPTION OF DRAWINGS

FIG. 9 is a schematic diagram of an air purification system according to a fifth exemplary embodiment that differs in a shape of a plasma generation zone from the other exemplary embodiments;

DESCRIPTION OF EXEMPLARY EMBODIMENTS

Exemplary embodiments of the present inventive concept are explained below with reference to accompanying drawings.

First Exemplary Embodiment

Figure 1:
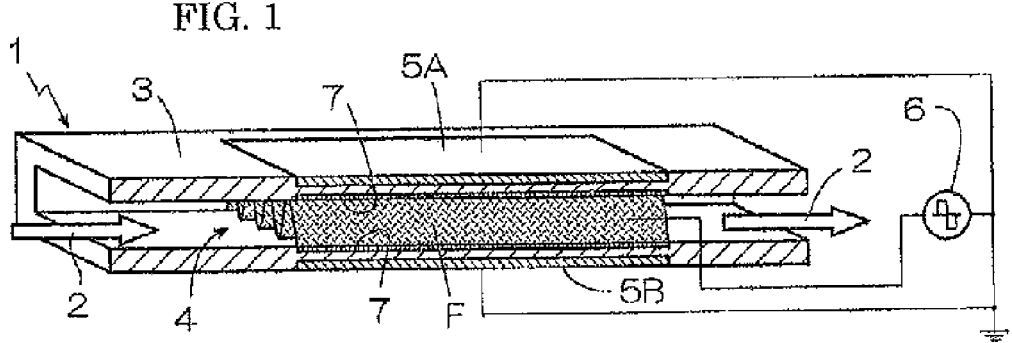
FIG. 1 is a schematic partial cut-away sectional diagram of an air purification system according to a first exemplary embodiment.
Figure 2:
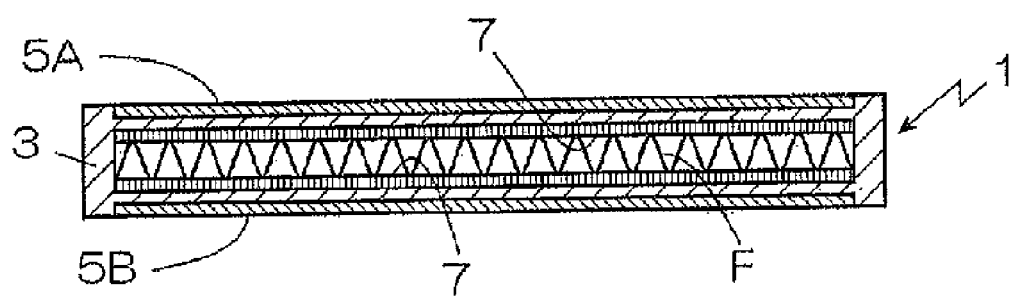
FIG. 2 is a schematic vertical sectional diagram of the air purification system shown in FIG. 1 when viewed from an air inlet side.

FIG. 1 is a schematic partial cut-away sectional diagram of an air purification system 1 according to a first exemplary embodiment, and FIG. 2 is a schematic vertical sectional diagram of the air purification system 1. The air purification system 1 includes a casing 3 made of an electrically non-conducting material and two plate-shaped electrodes 5A and 5B arranged on two opposing outer surfaces of the casing 3. The inside of the casing 3 is hollow and it constitutes an air passage 2 for passing air that needs to be purified. The electrodes 5A and 5B define a plasma generation zone 4 where plasma is generated in the air passage 2 within the casing 3.

A planar photocatalyst filter F is arranged in the plasma generation zone 4 such that it electrically contacts the opposing inner surfaces of the casing 3. A catalyst layer 7 (a catalyst body) is formed on one or both the inner surfaces of the casing 3 where the photocatalyst filter F touches the casing 3. The catalyst layer 7 can be a layer of platinum system, nickel system, oxide system depending on pollutants that need to be removed from the air. The catalyst layer 7 is made from a non-photoexcitation type catalyst.

The photocatalyst filter F is electrically connected to an alternate current (AC) voltage output terminal of an AC power supply 6, and the electrodes 5A and 5B are electrically connected to an earth terminal of the AC power supply 6. Thus, voltages of opposite polarities are applied to the photocatalyst filter F and the electrodes 5A and 5B. Consequently, the photocatalyst filter F and the electrodes 5A and 5B function as plasma generation electrodes that generate plasma.

More specifically, in the plasma generation zone 4, the casing 3 that is made of the electrically non-conducting material functions as a dielectric layer, and the photocatalyst filter F electrically contacts the casing 3 via the catalyst layer 7. Consequently, because the photocatalyst filter F and the electrodes 5A and 5B are separated only by the thickness of the casing 3, this arrangement makes it possible to generate a stable discharge between the two with a smaller electric power and current.

In addition, a higher safety can be achieved because the electrodes 5A and 5B that are exposed to the outside of the casing 3 are at the earth potential.

Figure 3:
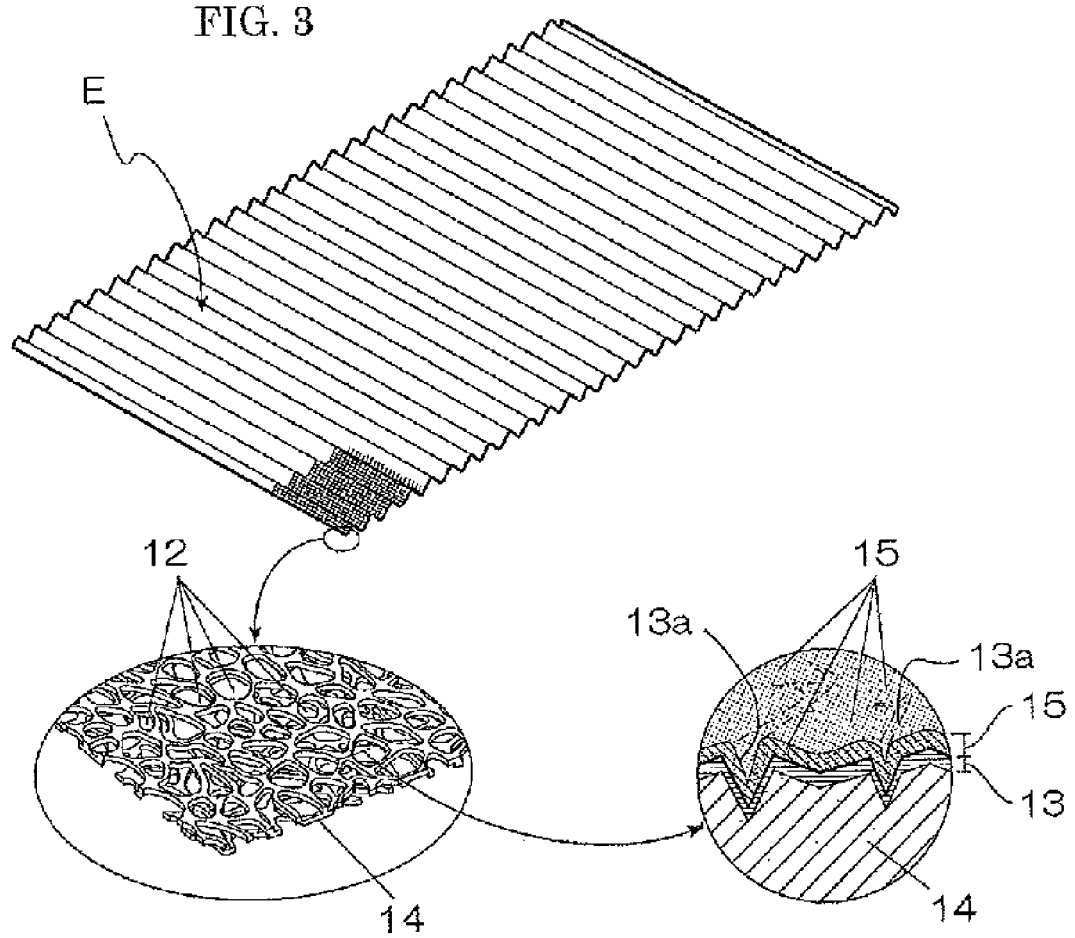
FIG. 3 is a schematic diagram for explaining a filter element that constitutes a photocatalyst filter shown in FIG. 1.

The photocatalyst filter F includes one or more filter elements. FIG. 3 is a schematic diagram for explaining a filter element E that constitutes the photocatalyst filter F. The filter element E is made of a titanium mesh 14. The titanium mesh 14 is prepared by making minute cavities 12 that function as air/water passages in a titanium foil 11 (See FIGS. 4A to 4G). A titanium oxide base layer 13 is formed on the titanium mesh 14 with an anodized film. A photocatalyst layer 15 is formed by baking anatase titanium dioxide particles on the titanium oxide base layer 13. The filter element E has an undulating structure. That is, the filter element E has alternating ridges and trenches that run continuously in one direction. The undulating structure can be periodic or non-periodic. Two or more filter elements can be stacked one above the other to form one photocatalyst filter F; in this case, however, it is preferable that at least one of the filter elements has the undulating structure. The undulating structure can be formed by press processing the titanium foil 11.

The ridges and trenches have such a height that when the photocatalyst filter F is inserted in the plasma generation zone 4, peaks of the ridges and trenches touch the opposing surfaces of the casing 3 or the catalyst layer 7. It is preferable that the ridges and trenches of the photocatalyst filter F have a substantially constant height (depth) to achieve better contact with the casing 3 or the catalyst layer 7 so that the photocatalyst filter F does not shift its position inside the casing 3.

The ridges and trenches can run in a direction of a central axis of the air purification system 1, in a direction orthogonal to the direction of the central axis of the air purification system 1, or in some other direction. The peaks of the ridges and trenches can be sharp or blunt.

FIGS. 4A to 4G depict a method of manufacturing the filter element E. First, etching processing is performed in order to form the minute cavities 12 in a flat non-porous titanium foil 11. The titanium foil 11 is obtained by rolling pure titanium. The etching processing includes a process of applying a photoresist material 16 on both the surfaces of the titanium foil 11 (see FIG. 4A), a process of overlaying a masking film 17 on which non-periodic patterns have been formed on the photoresist material 16 and exposing the photoresist material 16 (see FIG. 4B), a process of washing away the unexposed portions of the photoresist material 16 and causing the exposed portions of the photoresist material 16 to remain behind (see FIG. 4C), a process of dipping the titanium foil 11 with the non-periodic patterns masked thereon in etching liquid and corroding half of the titanium foil 11 from each surface in the thickness direction to form the minute cavities 12 that communicate from one surface to the other surface of the titanium foil 11. These processes result in the formation of the titanium mesh 14 (see FIG. 4D).

Figure 4A:
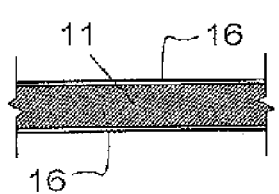
FIGS. 4A to 4G are explanatory views for explaining a method of manufacturing the photocatalyst filter shown in FIG. 3.
Figure 4B:
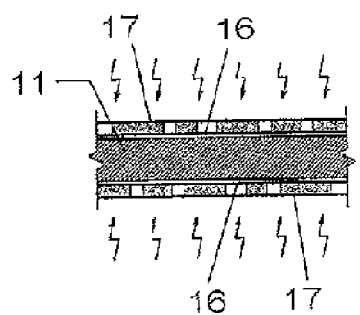
Figure 4C:
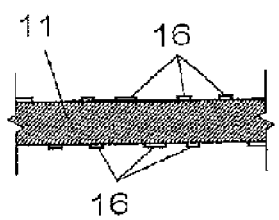
Figure 4D:
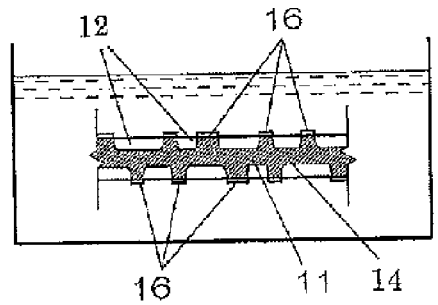
Figure 4E:
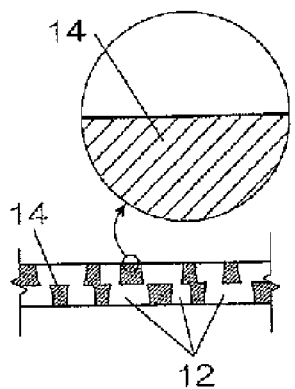

Particularly, performing the etching processing from both the surfaces of the titanium foil 11 is advantageous; because, it leads to the formation of a non-periodic spongy structure. In other words, when the etching processing is performed from both the surfaces of the titanium foil 11, minute cavities of different shapes and sizes are formed on each of the surfaces of the titanium foil 11. As a result, complicated labyrinth shaped minute cavities 12 shown in FIG. 2 are formed in the thickness direction of the titanium mesh 14 and a surface area is increased as compared to a simple mesh structure. The porosity of the titanium mesh 14 is between about 50% to about 80%. In an enlarged view, the surface of the titanium mesh 14 is substantially flat at this stage as shown in FIG. 4E.

Figure 4F:
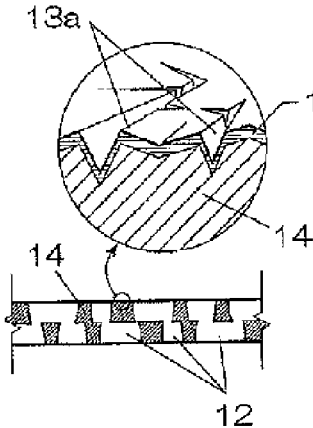

Subsequently, anodization processing for forming the titanium oxide base layer 13 on the surfaces of the titanium mesh 14 is performed. The anodization processing includes applying, in a phosphoric acid bath (for example, water containing 3% phosphoric acid), a voltage between the titanium mesh 14 as an anode and a not shown cathode. When the voltage is applied in this manner, as shown in FIG. 4F, the surface of the titanium mesh 14 is oxidized and an anodic oxide film is formed. The anodic oxide film is formed not only on the surface of the titanium mesh 14, but it is also formed on internal walls of the minute cavities 12. That is, the anodic oxide film is formed on every portion of the porous titanium foil 11 that is in contact with the liquid in the phosphoric acid bath. Subsequently, a heat treatment of heating the titanium mesh 14 in atmospheric conditions at 550 degree centigrade for three hours is performed. As a result, the anodic oxide film is converted into the titanium oxide base layer 13.

When the surface of the titanium mesh 14 is enlarged at this stage, a number of minute cracks 13a can be seen. These cracks were not present at the time point of completion of the etching processing, that is, the surface was substantially flat at that time point. In other words, the minute cracks 13a are developed due to the anodization processing and the heat treatment.

When titanium is subjected to anodic oxidation to form an anodic oxide film, the anodic oxide film produces a light having different colors due to interference depending on its thickness. For example, it is known that the anodic oxide film produces violet light when its thickness is about 70 nanometers (nm), green light when its thickness is about 150 nm, and pink light when its thickness is about 200 nm. In the first exemplary embodiment, an anodic oxide film having a thickness somewhere between 70 nm and 150 nm was formed.

Figure 4G:
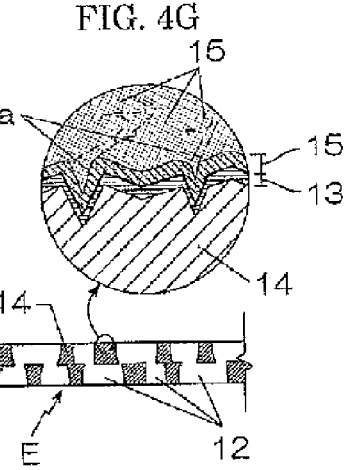

Finally, baking processing for attaching anatase titanium dioxide particles on the titanium oxide base layer 13 is performed to obtain the filter element E. More specifically, when the titanium mesh 14 with the titanium oxide base layer 13 formed thereon is dipped in a slurry containing the anatase titanium dioxide particles and the slurry is heated to about 550 degree centigrade, as shown in FIG. 4G, the photocatalyst layer 15 is formed on both the surfaces of the titanium mesh 14 and also on the internal walls of the minute cavities 12.

When the titanium oxide base layer 13 and the photocatalyst layer 15 are formed in this manner, there takes place an extremely strong binding between titanium oxides in each of these layers so that the photocatalyst layer 15 does not peel off easily.

Moreover, presence of the minute cavities 12 makes the surface of the titanium mesh 14 uneven with complicated bumps and holes. As a result, the minute cracks 13a of micron scale are formed in the titanium oxide base layer 13 that is the anodized film. Therefore, not only the photocatalyst layer 15 is bonded to it very strongly, but also the surface area is increased leading to an increase in the purification performance.

Furthermore, when the titanium mesh 14 is exposed to ultraviolet radiation, irregular reflection and/or scattering takes place at the boundary between the photocatalyst layer 15 and the titanium oxide base layer 13 whereby the ultraviolet radiation can be used more efficiently.

In addition, a photocatalyst sheet made of a titanium foil is lightweight and excellent in heat and chemical resistances. Therefore, it can be used even in harsh conditions.

In the first exemplary embodiment, in order to form the filter element E into an undulating shape, after performing the anodization processing and before performing the heat treatment, the filter element E is subjected to a forming processing of press machining to form the ridges and trenches. A pitch of ridges and trenches is, for example, about 5 millimeters and a height is, for example, 5 millimeters.

The filter element E obtained in this manner is inserted, as shown in FIGS. 1 and 2, in the plasma generation zone 4 of the air purification system 1 as the photocatalyst filter F such that the ridges and trenches run parallel to the direction of flow of the air in the air passage 2.

Figure 5:
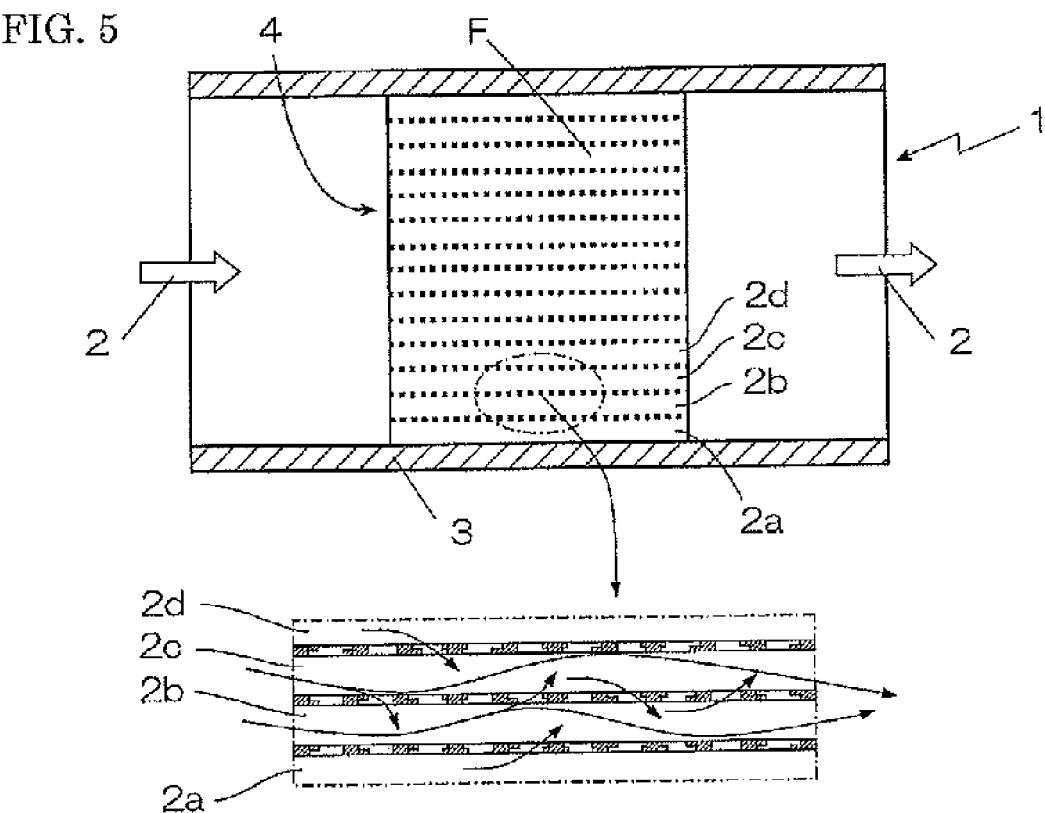
FIG. 5 is a schematic horizontal sectional diagram of the air purification system shown in FIG. 1 when viewed from above.

FIG. 5 is a schematic horizontal sectional diagram of the air purification system 1 when viewed from above. When the photocatalyst filter F is inserted in the air passage 2, due to the ridges and trenches of the photocatalyst filter F, the air passage 2 is divided into several parallel sub-air passages 2a, 2b, 2c, 2d and so on. As explained above, the photocatalyst filter F has the minute cavities 12 that function as air/water passages. When the air bumps onto the walls of the photocatalyst filter F in these sub-air passages, the air passes through these minute cavities 12 and enters into adjoining sub-air passages. This phenomenon leads to generation of complex air currents in the plasma generation zone 4 and increases the possibility of contact of the air with a photocatalyst in the photocatalyst filter F. When the air comes in contact with the photocatalyst, it is purified by the photocatalytic effect of the photocatalyst.

Although the titanium mesh 14 of the photocatalyst filter F is an electrical conductor, the titanium oxide base layer 13 that is the anodized film and the photocatalyst layer 15 that are formed on the surface of the titanium mesh 14 are electrical insulators. Therefore, in order to cause the photocatalyst filter F to function as a plasma generation electrode, power needs to be supplied to the titanium mesh 14.

The operation of the air purification system 1 is explained below. When a high-frequency voltage of specific value is applied from the AC power supply 6 to the various electrodes of the air purification system 1, an electric discharge occurs in the plasma generation zone 4. The air in the plasma generation zone 4 is converted into plasma at the room temperature and atmospheric pressure due to this electric discharge. Because the photocatalyst filter F is in contact with the casing 3, an electrode distance between the plasma generation electrodes of opposite polarities can be reduced and an effective electric discharge gap can be narrowed without physically making the plasma generation zone 4 narrow. Consequently, even when generating the plasma by a room pressure glow discharge, a stable electric discharge can be achieved with a low power, i.e., a smaller current. As a result, because there is no need to provide a large-scale power supply, the air purification system 1 can be mounted even in the home electric appliances.

Because the plasma is generated between the photocatalyst filter F and the electrodes 5A and 5B that are substantially planar, the plasma is generated substantially uniformly in the plasma generation zone 4. Consequently, the entire photocatalyst filter F is uniformly exposed to the plasma.

By generating the plasma by the room pressure glow discharge, which has higher plasma energy than the bonding energies of the pollutants generally contained in the atmospheric air, the pollutants in the air are decomposed in more than two molecules or atoms.

The room pressure plasma contains nitrogen and oxygen and it produces ultraviolet light that has several peaks within the wavelength range of about 300 nm to about 380 nm in which the titanium oxide photocatalyst is excited. Therefore, the plasma generated in the plasma generation zone 4 excites the photocatalyst in the photocatalyst filter F.

In a situation where the photocatalyst in the photocatalyst filter F is in the excited state, when air, room air or air inside a refrigerator, is passed through the plasma generation zone 4, the pollutants in the air are decomposed by the photocatalytic effect of the photocatalyst filter F and the air is converted into clean and odorless air.

The catalyst layer 7 made of the non-photoexcitation type catalyst is formed on one or both the inner surfaces of the casing 3. The air also touches the catalyst layer 7 when it passes through the air passage 2 and the pollutants in the air are oxidized and decomposed by the catalytic effect of the catalyst layer 7 and the air is converted into clean and odorless air.

Thus, the air is purified by the action of the plasma, by the action of the photocatalytic effect of the photocatalyst that is excited by the plasma, and by the action of the catalyst. That is, the air is purified simultaneously with three different purification methods. Consequently, even if the cubic capacity of the plasma generation zone has to be made smaller to make the air purification system compact, although the purification performance of the individual purification method may be lower due to the smaller size, the total purification performance will be higher.

Because the photocatalyst filter F is made of the titanium foil 11, it is flexible and it can be bent, curled, or rolled as per the requirement when used in the air purification system 1.

Moreover, because the photocatalyst filter F has the minute cavities 12, the photocatalyst filter F has a larger surface area as compared to a filter that has no minute cavities. Particularly, by forming a non-periodic spongy structure in the photocatalyst filter F, the surface area has been further increased. Consequently, more anatase titanium dioxide particles can be impregnated in the photocatalyst filter F leading to an increase in the purification performance.

Second Exemplary Embodiment

Figure 6:
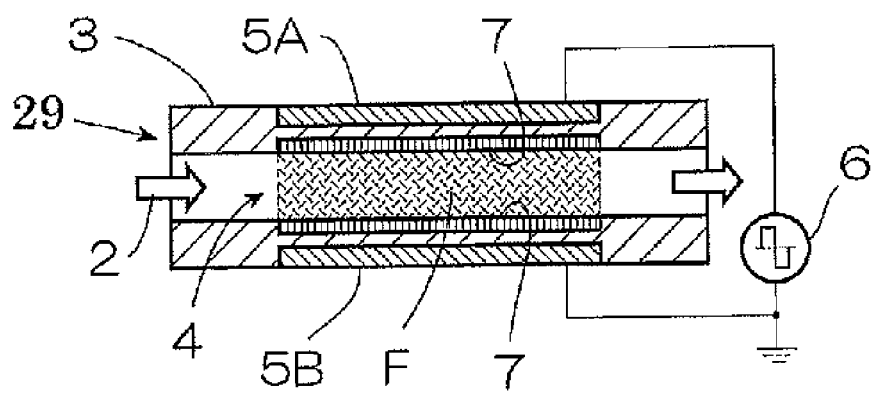
FIG. 6 is a schematic sectional diagram of an air purification system according to a second exemplary embodiment that differs in an electrical specification from the other exemplary embodiments.

FIG. 6 is a schematic sectional diagram of an air purification system 29 according to a second exemplary embodiment that differs in an electrical specification from the first exemplary embodiment. In the second exemplary embodiment, only the electrodes 5A and 5B are used as the plasma generation electrodes, i.e., the photocatalyst filter F is not used as the plasma generation electrode. That is, the electrodes 5A and 5B function as the plasma generation electrodes of opposite polarities.

Although the photocatalyst filter F is not used as the plasma generation electrode, because the photocatalyst filter F is in electrical contact with the casing 3, it will have the same electric potential as the electrodes 5A and 5B. Consequently, in the same manner as in the first exemplary embodiment, the electrode distance between the plasma generation electrodes of opposite polarities can be reduced and the effective electric discharge gap can be narrowed without physically making the plasma generation zone 4 narrow. As a result, the room pressure glow discharge can be achieved with a smaller power, i.e., a smaller current.

Even in the second exemplary embodiment, when air is passed through the plasma generation zone 4, the pollutants in the air are decomposed to more than two molecules or atoms due to the action of the plasma, and the air is converted into clean and odorless air. Furthermore, the air is purified by the action of the photocatalyst filter F and it is converted into clean and odorless air. Moreover, the air is purified by the action of the catalyst layer 7 and the air is converted into clean and odorless air.

Third Exemplary Embodiment

Figure 7:
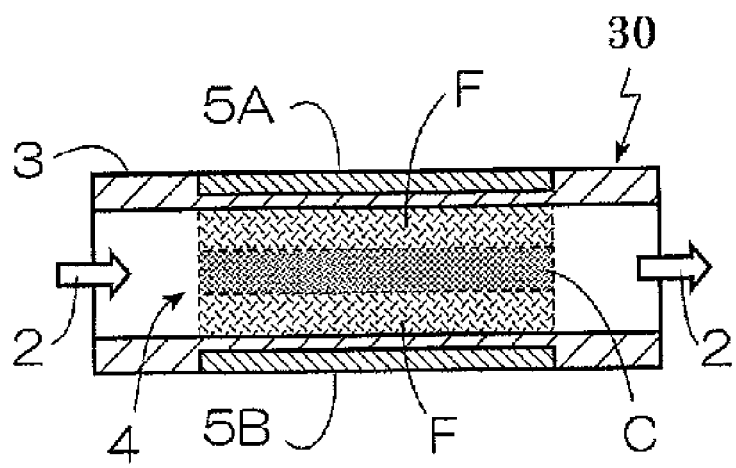
FIG. 7 is a schematic sectional diagram of an air purification system according to a third exemplary embodiment that differs in an arrangement of electrodes from the other exemplary embodiments.

FIG. 7 is a schematic sectional diagram of an air purification system 30 according to a third exemplary embodiment that differs in an arrangement of electrodes from the first and second exemplary embodiments. The same reference numbers/symbols have been used for components that have the same structure or that perform the same function as those shown in FIG. 1, and the explanation of those reference numbers/symbols have been omitted.

In the third exemplary embodiment, a catalyst filter C is arranged inside the plasma generation zone 4 in addition to the photocatalyst filter F. The catalyst filter C is impregnated with a non-photoexcitation type catalyst. The catalyst filter C includes a titanium mesh, or some other porous metal mesh, subjected to anodization processing, and the mesh is impregnated with the non-photoexcitation type catalyst. The catalyst can be platinum system, nickel system, oxide system depending on the pollutants that are to be removed from the air.

The catalyst filter C is arranged between two photocatalyst filters F. The photocatalyst filters F are in electric contact with the inner surfaces of the casing 3.

Consequently, in the third exemplary embodiment, the photocatalyst filters F and the electrodes 5A and 5B can be employed as the plasma generation electrodes, the catalyst filter C and the electrodes 5A and 5B can be employed as the plasma generation electrodes, or only the electrodes 5A and 5B can be employed as the plasma generation electrodes.

In the third exemplary embodiment, there are more chances that the air comes in contact with the catalyst in the catalyst filter C than in other exemplary embodiments. Thus, the air purification system 30 according to the third exemplary embodiment is more effective for purifying air that contains more pollutants that can be purified by the action of a non-photoexcitation type catalyst.

Fourth Exemplary Embodiment

Figure 8:
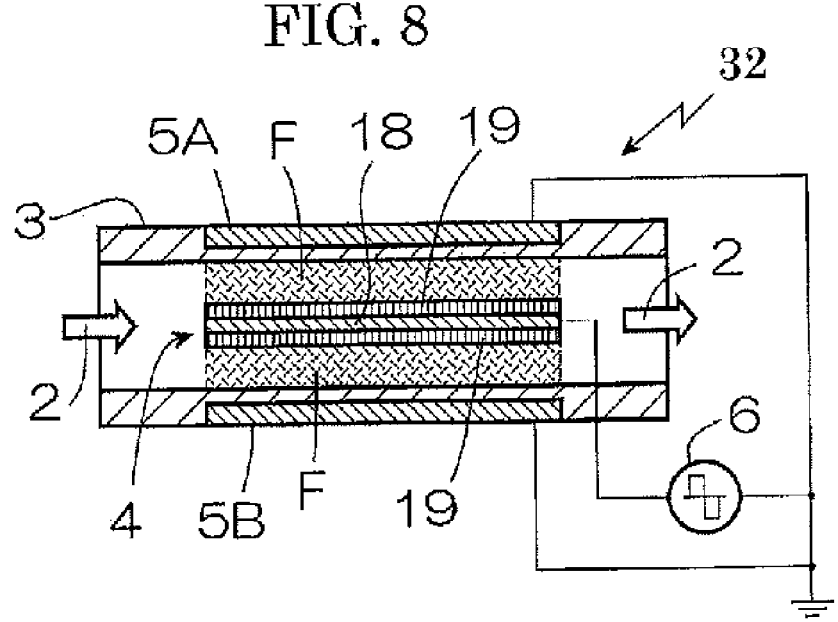
FIG. 8 is a schematic sectional diagram of an air purification system according to a fourth exemplary embodiment that differs in an arrangement of electrodes from the other exemplary embodiments.

FIG. 8 is a schematic sectional diagram of an air purification system 32 according to a fourth exemplary embodiment that differs in an arrangement of electrodes from the first to third exemplary embodiments. The same reference numbers/symbols have been used for components that have the same structure or that perform the same function as those shown in FIG. 1, and the explanation of those reference numbers/symbols have been omitted.

In the fourth exemplary embodiment, a metal plate 18 is arranged inside the plasma generation zone 4 in addition to the photocatalyst filter F. More specifically, the metal plate 18 is sandwiched between two photocatalyst filters F. Both the surfaces of the metal plate 18 are impregnated with a non-photoexcitation type catalyst.

Consequently, in the fourth exemplary embodiment, the metal plate 18 and the electrodes 5A and 5B are employed as the plasma generation electrodes of opposite polarities.

Fifth Exemplary Embodiment

FIG. 9 is a schematic diagram of an air purification system 21 according to a fifth exemplary embodiment that differs in a shape of the plasma generation zone from the first to fourth exemplary embodiments. The air purification system 21 includes a cylindrical casing 23 made of an electrically conducting material that forms a plasma generation zone 22. A rolled photocatalyst filter F2 is arranged inside the cylindrical casing 23. More specifically, one undulating filter element E and one flat (non-undulating) filter element E2 are overlapped and then rolled to obtain the photocatalyst filter F2. Two plasma generation electrodes 24A and 24B are provided. The electrode 24A is arranged on an outer surface of the cylindrical casing 23 and it is electrically connected to the AC voltage output terminal of the AC power supply 6, and the electrode 24B is connected to the earth terminal of the AC power supply 6. The photocatalyst filter F2 functions as the other electrode 24B and it is electrically connected to the AC voltage output terminal of the AC power supply 6. The catalyst layer 7 of the non-photoexcitation type catalyst is formed on an inner surface of the cylindrical casing 23 where the photocatalyst filter F2 touches the cylindrical casing 23. The catalyst layer 7 is optional.

When a high-frequency voltage of specific value is applied from the AC power supply 6 to the electrodes 24A and 24B, the electrodes 24A and 24B function as plasma generation electrodes of opposite polarities and an electric discharge occurs in the plasma generation zone 22. The air in the plasma generation zone 22 is converted into plasma at the room temperature and atmospheric pressure due to this electric discharge. Because the photocatalyst filter F2 is in contact with the cylindrical casing 23, the electrode distance between the plasma generation electrodes of opposite polarities can be reduced and the effective electric discharge gap can be narrowed without physically making the plasma generation zone 22 narrow. Consequently, because there is no need to provide a large-scale power supply, the air purification system 21 can be mounted even in the home electric appliances.

When air, room air or air inside a refrigerator, is passed through the plasma generation zone 22, the pollutants in the air are decomposed in more than two molecules or atoms by the action of the plasma generated in the plasma generation zone 22 and the air is converted into clean and odorless air. The air is also purified by the action of the photocatalyst that is excited by the plasma, and the polluted air is converted into clean and odorless air. The air is also purified by the action of the catalyst in the catalyst layer 7 and converted into clean and odorless air.

Sixth Exemplary Embodiment

Figure 10A:
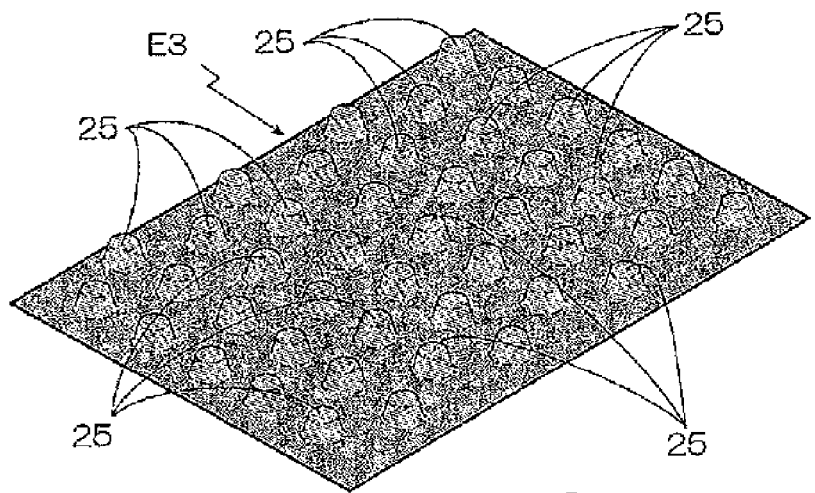
FIGS. 10A and 10B are schematic diagrams of a filter element according to a sixth exemplary embodiment.
Figure 10B:
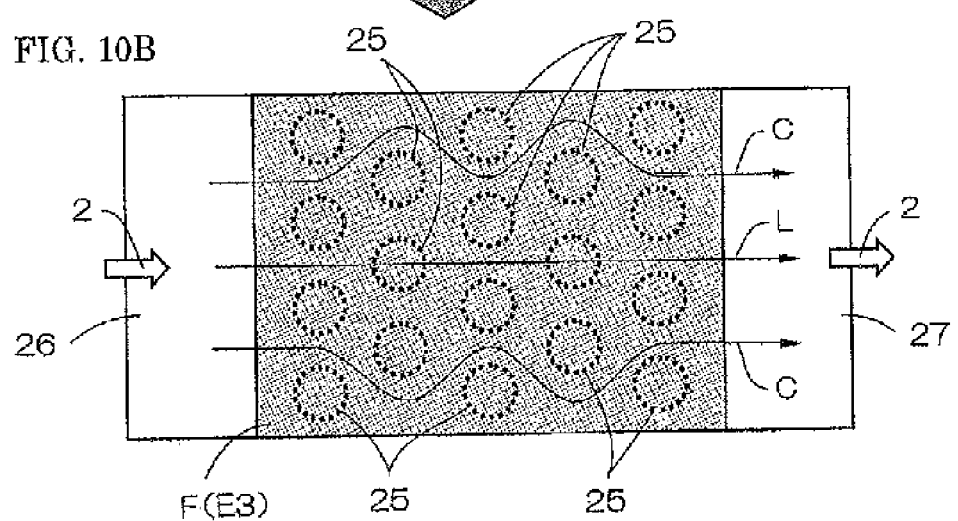

In all the first to fifth exemplary embodiments described above, the filter element E had an undulating structure; however, the structure of the filter element E is not limited to the undulating structure. FIGS. 10A and 10B are schematic diagrams of a filter element E3 according to a sixth exemplary embodiment. As shown in FIG. 10A, the filter element E3 is provided with protrusions 25 so as to cause disturbance in the air flow and generate complicated air currents. The protrusions 25 can be formed by press processing. The density of the protrusions 25 can be set as desired.

The filter elements in the other exemplary embodiments can be replaced with the filter element E3. For example, when the filter element E3 is used in the air purification system 1 of the first exemplary embodiment, as shown in FIG. 10B, when air enters into the air passage 2 from an air inlet 26 and the air is discharged from an air outlet 27, the air inevitably bumps into the protrusions 25, irrespective of whether the air takes a straight path L or meandering paths C. As a result, complex air currents are produced in the plasma generation zone 4 and the chances that the air comes in contact with the photocatalyst of the filter element E3 are greatly increased. In addition, because the air does not pass through the minute cavities in the filter element E3 when it takes the meandering paths C, the pressure loss is low. Consequently, more air can be purified leading to an increase in the processing efficiency of the air purification system.

Seventh Exemplary Embodiment

Figure 11A:
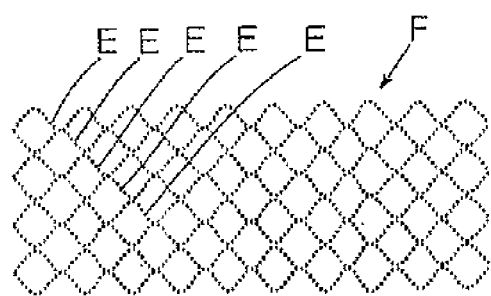
FIGS. 11A and 11B are schematic diagrams of a photocatalyst filter according to a seventh exemplary embodiment.
Figure 11B:
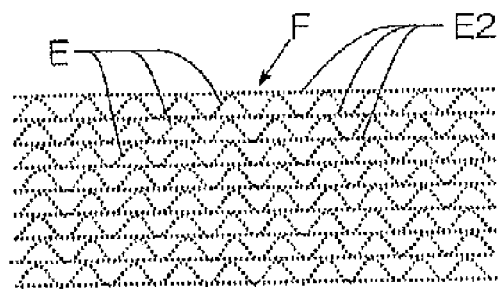

The photocatalyst filter F can include a plurality of filter elements. FIGS. 11A and 11B are schematic diagrams of the photocatalyst filter F according to a seventh exemplary embodiment. The photocatalyst filter F shown in FIG. 11A includes a plurality of the undulating filter elements E stacked above one another. The photocatalyst filter F shown in FIG. 11B includes a plurality of the undulating filter elements E and a plurality of flat filter elements E2 stacked above one another in an alternating manner. The number of filter elements in the photocatalyst filter F can be decided based on the size of the plasma generation zone 4.

Eighth Exemplary Embodiment

Figure 12:
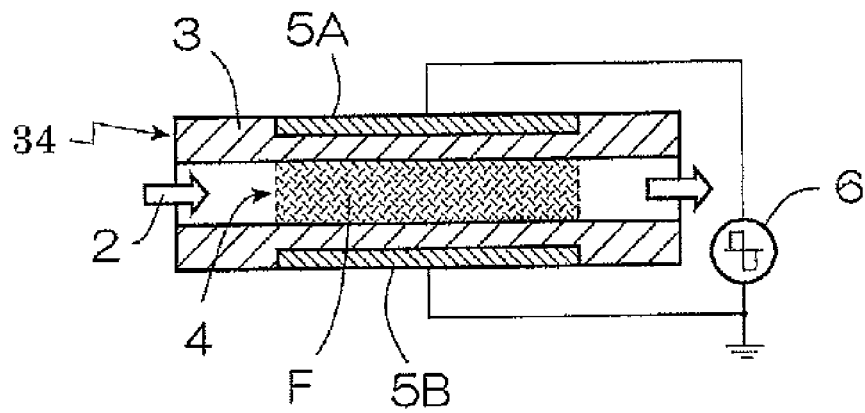
FIG. 12 is a schematic vertical sectional diagram of an air purification system according to an eighth exemplary embodiment.

FIG. 12 is a schematic vertical sectional diagram of an air purification system 34 according to an eighth exemplary embodiment. The air purification system 34 has a simple structure in which the photocatalyst filter F is sandwiched between the electrodes 5A and 5B that define the plasma generation zone 4, and the electrodes 5A and 5B are connected to the opposite terminals of the AC power supply 6.

When air, room air or air inside a refrigerator, is passed through the plasma generation zone 4, the pollutants in the air are decomposed in more than two molecules or atoms by the action of the plasma generated in the plasma generation zone 4 and the air is converted into clean and odorless air. The air is also purified by the photocatalytic effect of the photocatalyst that is excited by the plasma, and the polluted air is converted into clean and odorless air. Because the air purification system 34 does not include a non-photoexcitation type catalyst layer, the air purification system 34 is more effective for purifying air that contains more pollutants that can be purified by the action of a photocatalyst than pollutants that can be purified by the action of a catalyst.

FIGS. 13A to 13D are graphs depicting experimental results obtained with the air purification system 34. In these experiments, the air purification system 34 was put inside a 1-cubic-meter acryl chamber and a certain number of cigarettes were burnt inside the chamber to fill the chamber with cigarette smoke. Then, the air in the chamber was subjected to purification processing by using the air purification system 34, and a temporal change in the concentrations of various odiferous components inside the chamber was measured.

Figure 13A:
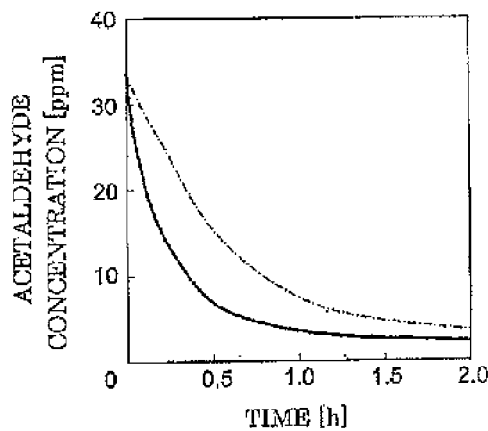
FIGS. 13A to 13D are graphs depicting experimental results obtained with the air purification system according to the eighth exemplary embodiment.
Figure 13B:
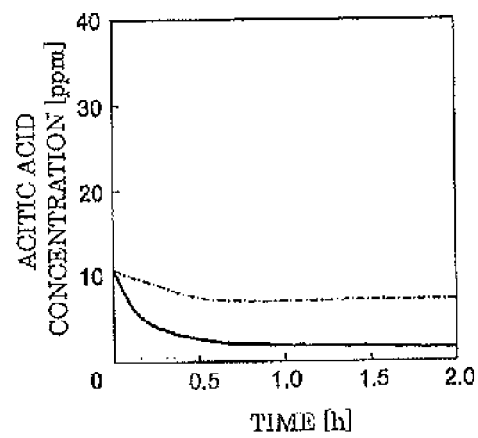
Figure 13C:
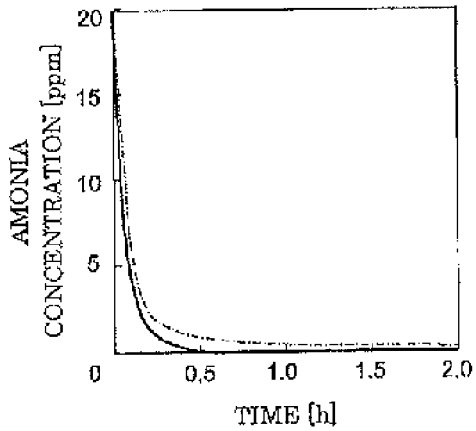
Figure 13D:
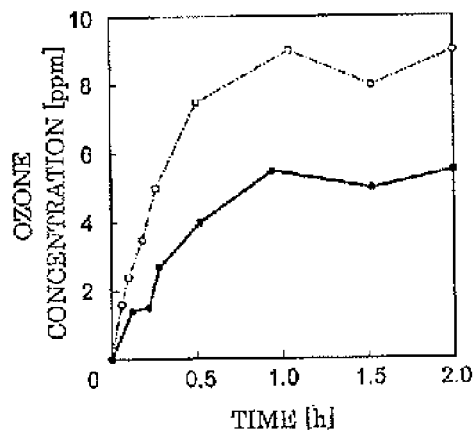

In FIGS. 13A to 13C, solid lines depict a temporal change in the concentrations of acetaldehyde, acetic acid, and ammonia. In FIG. 13D, a solid line depicts a temporal change in the concentrations of ozone that is generated due to generation of plasma. Similar experiment was performed by using a comparative air purification system having no photocatalyst filter. In FIGS. 13A to 13D, non-continuous lines depict the experimental results obtained with the comparative air purification system.

As can be seen from these experimental results, the processing efficiency of the air purification system 34 for acetaldehyde, acetic acid, and ammonia is higher than that of the comparative air purification system. In addition, generation of ozone is suppressed to as much as ½.

As explained above, in the air purification systems according to the first to eighth exemplary embodiments, the photocatalyst filter is arranged in the plasma generation zone that constitutes the air passage for air that is to be purified. The photocatalyst filter includes one or more filter elements that are made as follows. That is, numerous minute cavities that function as air passages are formed in the titanium foil, and the titanium oxide base layer is formed on the titanium mesh with the anodized film to obtain the titanium mesh. Finally, the photocatalyst layer is formed by baking anatase titanium dioxide particles on the titanium oxide base layer to obtain the filter element. At least one of the filter elements has the undulating structure.

The layer of the non-photoexcitation type catalyst is provided on the inner surfaces of the plasma generation zone, or a catalyst member made of the non-photoexcitation type catalyst is arranged inside the plasma generation zone.

The plate-shaped electrodes are provided along the air passage. The photocatalyst filter is arranged inside the plasma generation zone and the electrodes are electrically connected to the terminals of opposite polarities of the AC power supply. Thus, the photocatalyst filter and the electrode function as the plasma generation electrodes.

The layer of the electrically conducting material is provided between the electrodes in the plasma generation zone.

The peaks of undulations of the filter element are in electrical contact with the conducting material.

The plasma generation zone is provided inside the cylindrical casing, and the filter element is rolled and arranged in the plasma generation zone. The plate-shaped electrode is provided on the outer periphery of the cylindrical casing. The photocatalyst filter arranged inside the plasma generation zone and the electrode are electrically connected to the terminals of opposite polarities of the AC power supply. Thus, the photocatalyst filter and the electrode function as plasma generation electrodes.

The plate-shaped electrodes are provided on either sides of the air passage. These electrodes are electrically connected to the terminals of opposite polarities of the AC power supply. Thus, the electrodes function as plasma generation electrodes.

The undulating structure includes alternating ridges and trenches that run continuously in one direction of the filter element.

The undulating structure includes the protrusions arranged in a matrix.

The photocatalyst filter includes a plurality of filter elements having the undulating structure and a plurality of filter elements having the non-undulating structure stacked above one another in an alternating manner.

The titanium mesh has the non-periodic spongy structure formed by performing etching processing on the titanium foil from one or both of its surfaces by using non-periodic patterns.

Ninth Exemplary Embodiment

As explained above, in the air purification systems according to the first to eighth exemplary embodiments, the photocatalyst filter is arranged inside a confined plasma generation zone and air that needs to be purified is passed through this confined plasma generation zone. For example, in the air purification system 1 shown in FIG. 1, the plasma generation zone 4 is inside the casing 3, and the photocatalyst filter F is arranged in the plasma generation zone 4. Moreover, in the air purification system 21 shown in FIG. 9, the plasma generation zone 22 is inside the cylindrical casing 23, and the photocatalyst filter F2 is arranged in the plasma generation zone 22.

The air does not pass easily in the confined plasma generation zone so that some sort of pressure difference needs to be created on the entry and exit sides of the air of the plasma generation zone. Moreover, water is produced as a byproduct in the process of purification of the air by the action of the photocatalyst. The water is deposited on the photocatalyst filter and degrades its purification efficiency. Moreover, the confined plasma generation zone is filled with water vapor and this further hinders the flow of air in the plasma generation zone again degrading the purification efficiency. In addition, arranging the photocatalyst filter inside the casing in the plasma generation zone is a difficult task. Thus, there is a room for development in the air purification systems according to the above exemplary embodiments.

Figure 14:
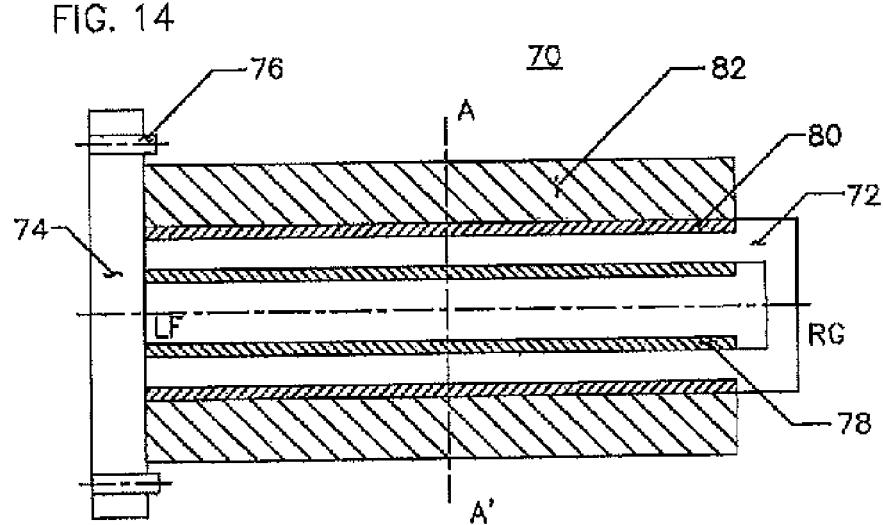
FIG. 14 is a schematic sectional diagram of an air purification system according to a ninth exemplary embodiment that differs in a position of a photocatalyst filter from the other exemplary embodiments.
Figure 15:
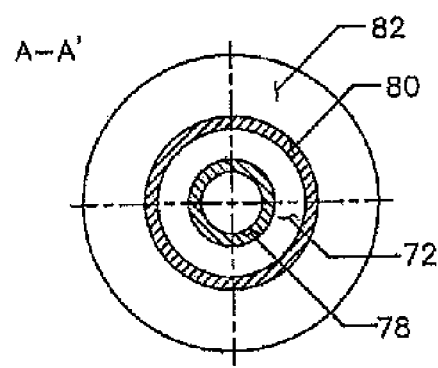
FIG. 15 is a schematic sectional diagram of the air purification system along a line A-A' shown in FIG. 14.
Figure 16:
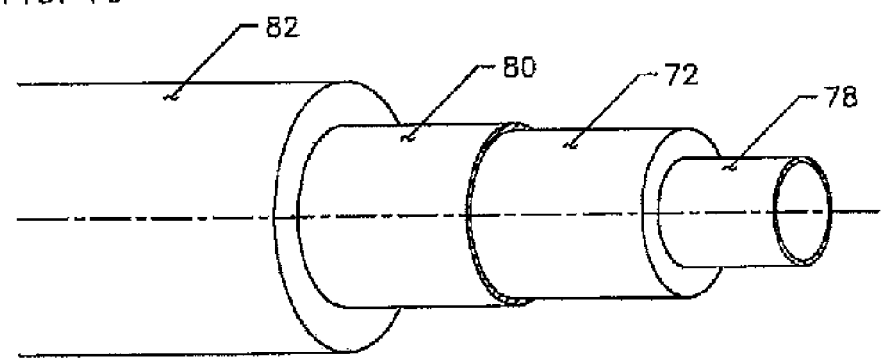
FIG. 16 is a schematic perspective diagram of the air purification system shown in FIG. 14.
Figure 17:
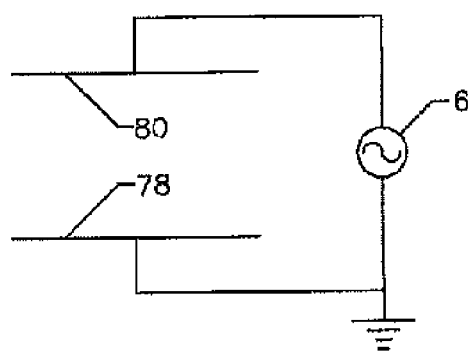
FIG. 17 is a schematic diagram showing an electrical specification of the air purification system shown in FIG. 14.

FIG. 14 is a schematic sectional diagram of an air purification system 70 according to a ninth exemplary embodiment, FIG. 15 is a schematic sectional diagram of the air purification system 70 along a line A-A', FIG. 16 is a schematic perspective diagram of the air purification system 70, and FIG. 17 is a schematic diagram showing an electrical specification of the air purification system 70.

As shown in FIG. 14, the air purification system 70 includes a cylindrical casing 72 that is attached to a base member 74. The casing 72 and the base member 74 are made of ceramic that is an electrical non-conducting material. The base member 74 is attached with attaching members 76 to a member of a device, such as a refrigerator, air conditioner, vacuum cleaner, humidifier, dehumidifier, in which the air purification system 70 is to be used. The attaching members 76 are, for example, screws. Meanwhile, the base member 74 can be adhered to the member instead of using the attaching members 76.

An end LF of the casing 72 is attached to the base member 74. The other end RG of the casing 72 is closed. However, this structure is not mandatory. For example, the end RG can be open, or the end RG can be attached to a not shown base member.

As shown in FIGS. 14, 15, and 16, the inside of the casing 72 is hollow. A plate-shaped inner electrode 78 is provided on an inner surface of the casing 72. The entire inner surface of the casing 72 or only a part thereof can be covered with the inner electrode 78.

A plate-shaped outer electrode 80 is provided on an outer surface of the casing 72. The entire outer surface of the casing 72 or only a part thereof can be covered with the outer electrode 80.

A photocatalyst filter 82 is arranged on an outer surface of the outer electrode 80. The photocatalyst filter 82 can be the photocatalyst filter F or the photocatalyst filter F2.

As shown in FIG. 17, the inner electrode 78 and the outer electrode 80 are electrically connected to the electrodes of opposite polarities of the AC power supply 6. Thus, the inner electrode 78 and the outer electrode 80 that sandwich the casing 72, which is a non-conductor, function as the plasma generation electrodes. When the AC power supply 6 is turned on, an electric discharge occurs between the inner electrode 78 and the outer electrode 80 and air present around the inner electrode 78 and the outer electrode 80 is converted into plasma at the room temperature and atmospheric pressure due to this electric discharge.

Although not specifically shown in the drawings, the outer electrode 80 can be omitted. That is, the photocatalyst filter 82, which is an electrically conducting member, can be directly provided on the outer surface of the casing 72. In this configuration, the inner electrode 78 and the photocatalyst filter 82 function as the plasma generation electrodes.

Thus, in the air purification system 70, a plasma generation zone is on both inner and outer sides of the casing 72. The photocatalyst filter 82 is arranged in the plasma generation zone that is on the outer side of the casing 72 where the plasma generation zone is open, i.e., not confined. Because the plasma generation zone is open, air can freely flow into and out of the plasma generation zone and the air can be purified with the action of the photocatalyst in the photocatalyst filter 82. Moreover, water produced as a byproduct in the process of purification of the air by the photocatalyst is evaporated, i.e., the water does not deposit on the photocatalyst filter 82. Furthermore, water vapor is easily carried away with the purified air so that the water vapor does not hinder the flow of air in the plasma generation zone. All these facts lead to an increase in the purification efficiency.

In addition, a task of arranging a photocatalyst filter outside a casing is easier than a task of arranging a photocatalyst filter inside the casing. This fact makes the manufacturing of the air purification system 70 easier than the manufacturing of the air purification system 1 or 21.

Figure 18A:
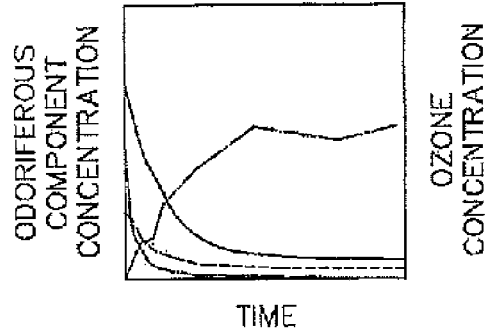
FIGS. 18A, 18B, 19A, 19B, and 20 are graphs depicting experimental results according to the ninth exemplary embodiment.

FIG. 18A is a graph depicting experimental results obtained with the air purification system 70. In this experiment, the air purification system 70 was put inside a 1-cubic-meter acryl chamber and five cigarettes were burnt in the chamber to fill the chamber with cigarette smoke. Then, the air in the chamber was subjected to purification processing by using the air purification system 70, and a temporal change in the concentrations of various odiferous components inside the chamber was measured. In FIG. 18A, a solid line depicts a temporal change in the concentrations of acetaldehyde, a dashed line depicts a temporal change in the concentrations of acetic acid, and a one-point dashed line depicts a temporal change in the concentrations of ammonia. In FIG. 18A, a two-point dashed line depicts a temporal change in the concentrations of ozone that is generated due to generation of plasma.

Figure 18B:
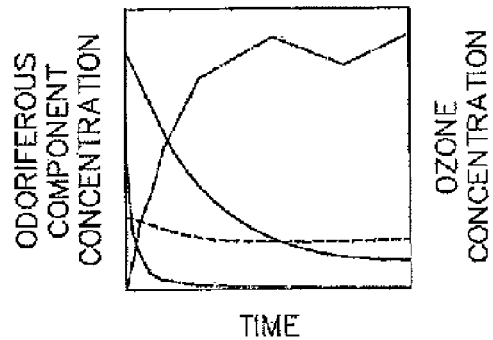

A similar experiment was performed by using a comparative air purification system having no photocatalyst filter. FIG. 18B is a graph depicting experimental results obtained with the comparative air purification system. As can be seen from these experimental results, the processing efficiency of the air purification system 70 for acetaldehyde, acetic acid, and ammonia is higher than that of the comparative air purification system. In addition, generation of ozone is suppressed to as much as ½.

Figure 19A:
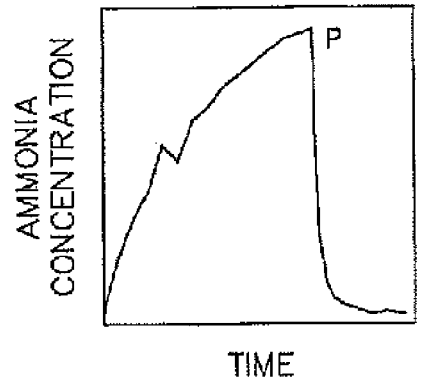

FIG. 19A is a graph depicting experimental results obtained when the air purification system 70 is assumed to be used in animal experimentation facility. In this experiment, the air purification system 70 was put inside a 1-cubic-meter acryl chamber and 30 milliliters of ammonia water was put in the chamber as an ammonia source. Then, the air in the chamber was subjected to purification processing by using the air purification system 70, and a temporal change in the concentrations of ammonia inside the chamber was measured. In FIG. 19A, the AC power supply 6 of the air purification system 70 was turned on at a point P in time. It can be seen from FIG. 19A that the concentrations of ammonia dropped drastically from the point P, which proves that the air purification system 70 was effective in decomposing ammonia.

Figure 19B:
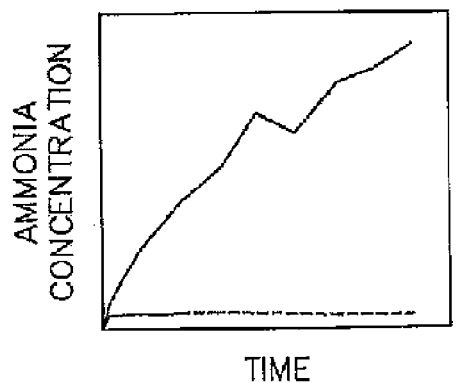

Similar experiments as that explained with reference to FIG. 19A were performed with the AC power supply 6 always on and always off, respectively. The results are shown in FIG. 19B in which a solid line depicts a temporal change in the concentrations of ammonia when the AC power supply 6 was always off and a dashed line depicts a temporal change in the concentrations of ammonia when the AC power supply 6 was always on. It can be seen from FIG. 19B that the air purification system 70 is very effective in decomposing ammonia. Moreover, the air purification system 70 is very effective in decomposing ammonia even when the ammonia is produced continuously.

Figure 20:
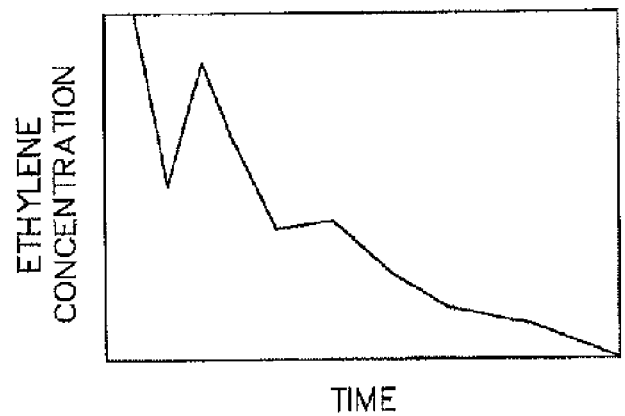
Figure 21:
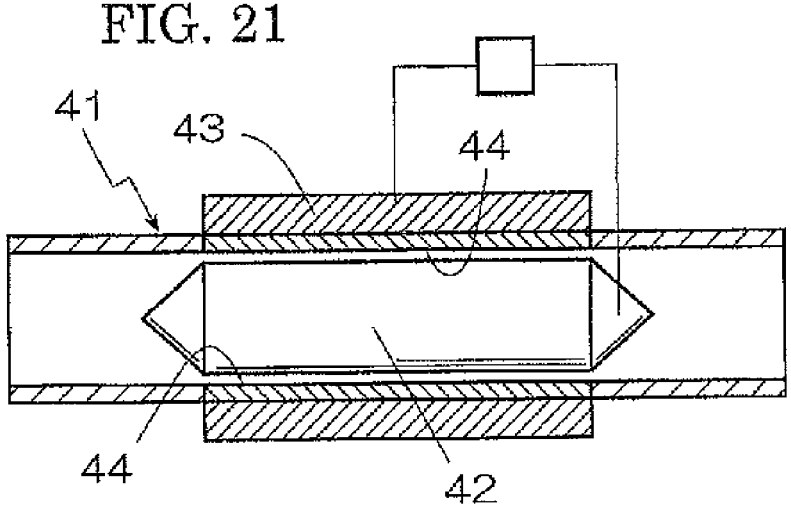
FIG. 21 is a schematic sectional diagram of a conventional air purification system.
Figure 22:
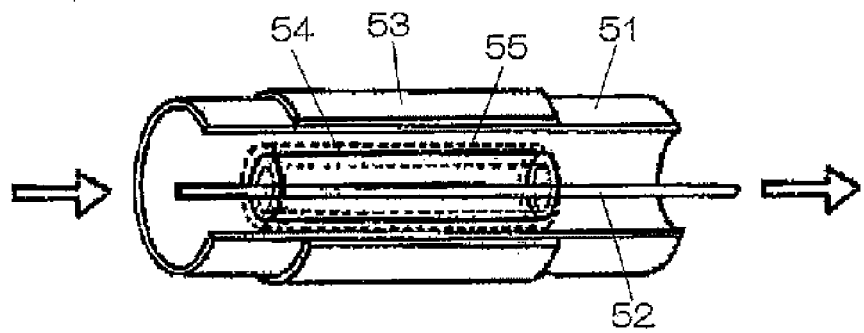
FIG. 22 is a schematic perspective diagram of the conventional air purification system.

FIG. 20 is a graph depicting experimental results obtained when the air purification system 70 is assumed to be used in a refrigerator to preserve freshness inside the refrigerator. In this experiment, the air purification system 70 was put inside a 1-cubic-meter acryl chamber and the chamber was filled with ethylene gas. Then, the air in the chamber was subjected to purification processing by using the air purification system 70, and a temporal change in the concentrations of ethylene gas inside the chamber was measured. It can be seen from FIG. 20 that the air purification system 70 was effective in decomposing the ethylene gas.

As explained above, in the air purification system according to the ninth exemplary embodiment, the photocatalyst filter is arranged outside the casing and the plasma generation zone is open. This arrangement leads to an increase in the purification efficiency and improved manufacturing ease.

INDUSTRIAL APPLICABILITY

The air purification systems according to the exemplary embodiments can be suitably mounted and used in home electric appliances such as refrigerators, air conditioners, vacuum cleaners, humidifiers, and dehumidifiers.

Explanations of Letters or Numerals

1 Air purification system
2 Air passage
3 Casing
4 Plasma generation zone
5A, 5B Electrode
F Photocatalyst filter
6 AC power supply
7 Catalyst layer
11 Titanium foil
12 Minute cavities
13 Titanium oxide base layer
14 Titanium mesh
15 Photocatalyst layer
E Filter element
70 Air purification system
72 Casing
78, 80 Electrode
82 Photocatalyst filter

We claim:

1. An air purification system comprising:
    an internally hollow cylindrical supporting member made of an electrically non-conducting material;
    an inner electrode arranged on an inner surface of the supporting member;
    a photocatalyst filter arranged on an outer surface of the supporting member for purifying air inside a plasma generation zone by an action of a photocatalyst, the photocatalyst filter being made of an electrically conducting material; and
    a power source for supplying power of opposite polarities to each of the inner electrode and the photocatalyst filter so as to generate plasma by producing an electric discharge between the inner electrode and the photocatalyst filter, wherein
    the photocatalyst filter includes a filter element, and the filter element includes a porous titanium foil having a non-periodic spongy structure impregnated with anatase titanium dioxide particles as a photocatalyst.

2. The air purification system according to claim 1, wherein the photocatalyst filter includes a plurality of filter elements.

3. The air purification system according to claim 1, wherein the photocatalyst filter includes a plurality of flat and undulating filter elements arranged alternately.

4. The air purification system according to claim 3, wherein the undulating filter element is formed by press processing the porous titanium foil.

* * * * *